US 8,223,011 B2

(12) United States Patent
Noury et al.

(10) Patent No.: US 8,223,011 B2
(45) Date of Patent: Jul. 17, 2012

(54) PROCESSES AND SYSTEM FOR DETECTION OF ABNORMAL SITUATIONS OF A PERSON IN A LIVING SPACE

(75) Inventors: Norbert Noury, Grenoble (FR); Jean-Eric Lundy, Thiais (FR); Vincent Rialle, Saint Egreve (FR)

(73) Assignees: Vigilio, Evry (FR); Universite Joseph Fourier-Grenoble 1, St. Martin d'Heres (FR)

( * ) Notice: Subject to any disclaimer, the term of this patent is extended or adjusted under 35 U.S.C. 154(b) by 664 days.

(21) Appl. No.: 12/443,544

(22) PCT Filed: Sep. 28, 2007

(86) PCT No.: PCT/EP2007/060320
§ 371 (c)(1), (2), (4) Date: Mar. 30, 2009

(87) PCT Pub. No.: WO2008/037797
PCT Pub. Date: Apr. 3, 2008

(65) Prior Publication Data
US 2010/0007502 A1 Jan. 14, 2010

(30) Foreign Application Priority Data
Sep. 29, 2006 (FR) .................................. 06 08584

(51) Int. Cl.
*G08B 1/08* (2006.01)
(52) U.S. Cl. .......... 340/539.12; 340/539.1; 340/539.11; 340/573.1
(58) Field of Classification Search ............... 340/539.1, 340/539.12
See application file for complete search history.

(56) References Cited

U.S. PATENT DOCUMENTS

| 6,160,478 A | 12/2000 | Jacobsen et al. |
| 6,201,476 B1 | 3/2001 | Depeursinge et al. |
| 6,433,690 B2 | 8/2002 | Petelenz et al. |
| 6,524,239 B1 * | 2/2003 | Reed et al. .................... 600/300 |
| 2006/0089538 A1 * | 4/2006 | Cuddihy et al. .............. 600/300 |

FOREIGN PATENT DOCUMENTS

| CA | 2 529 545 A1 | 6/2006 |
| EP | 0 877 346 A1 | 11/1998 |
| EP | 1 128 349 A1 | 8/2001 |
| GB | 2 401 466 A | 11/2004 |
| WO | WO 98/29852 | 7/1998 |
| WO | WO 99/56262 | 11/1999 |
| WO | WO 03/044755 A1 | 5/2003 |
| WO | WO 2004/100092 A2 | 11/2004 |
| WO | WO 2006/000605 A1 | 1/2006 |

* cited by examiner

*Primary Examiner* — Travis Hunnings
(74) *Attorney, Agent, or Firm* — Pauley Petersen & Erickson

(57) ABSTRACT

Method and system for detecting abnormal situations of a person in a living place. One such method involves: receiving information provided by a sensor carried by the person, which information relates to at least one vital variable of the person, receiving information originating from a series of motion sensors provided at various locations in the living place, and comparing said information with predetermined rules involving timeouts established as a function of the location and of the period of the day, or else different timeouts depending on whether an anomaly has been detected at the level of the vital variable, or else according to a common process relaunched upon each arrival in a new location although no abnormal situation exists, and in response to the previous step, triggering or otherwise a signalling of abnormal situation. Application in particular to the telesurveillance of the elderly, with improved discrimination between normal, anomalous and alert situations.

19 Claims, 2 Drawing Sheets

PROCESSES AND SYSTEM FOR DETECTION OF ABNORMAL SITUATIONS OF A PERSON IN A LIVING SPACE

The present invention relates in general to detection systems, especially for remote surveillance of elderly people.

It relates more particularly to a refined system with an improved "confirmation" relative to existing systems, that is which permits better discrimination between the veritable anomalies such as a person having had a fall, and different actions or situations of the daily life which can be detected while the person is not in danger.

More particularly still, the invention aims to reinforce the sensitivity and the specificity of a sensor of a vital variable of the person, such as a fall sensor, worn by the person combining an indication detected by such a sensor with information supplied by other sensors carried out in the environment of the person.

It is known that a sensor such as a fall sensor, a cardiac rhythm sensor, etc., worn by the person, cannot by itself offer maximal reliability in the face of the various situations that can occur and which are sources of:

"False negatives": for example some falls are not detectable because they do not result from a movement of significant amplitude, whereas the person is incapable of standing up again without aid (faintness);

"False positives": again, with a fall detector, some movements reach an unusual intensity without however keeping the person from getting up unaided (for example stumbling, letting oneself fall in bed).

The performance of a fall sensor can thus be appreciated only by factors of sensitivity (capacity of the system to detect all falls) and of specificity (capacity of the system to detect falls only).

Yet, a fall can take many forms (forwards, backwards, sideways, straight or with rotation of the body, ending up in a prostrate or seated position, etc.). It is therefore practically impossible to test a fall sensor exhaustively. Furthermore, the same falling movement, even the simplest (for example a rear fall after slipping) can occur variably following the context and the subject. Consequently, it is not possible to attain total sensitivity (no false negatives) and total specificity (no false positives) with reasonable fall detection means in terms of bulk, complexity and cost. The same type of problem can be encountered with a cardiac rhythm sensor, where a situation can be normal in one context and alarming in another.

It is also known to further improve the performance of a sensor such as a fall sensor by combining the information it delivers with information of a geographical or temporal nature (GPS geolocalisation, duration of immobilisation, etc.).

Documents EP 0 877 346, U.S. Pat. Nos. 6,201,476, 6,160, 478, 6,433,690, WO 2006/000605, WO 2004/100092, EP 1 128 349, WO 98/29852 and WO 99/56262 will be cited in particular.

The present invention aims to at least in part eliminate these limitations of the prior art and to propose a process and a system which especially execute improved discrimination, dictated at the same time by the contexts of place and time, of normal, abnormal and alert situations in response to vital information supplied by a sensor worn by the person, preferably without increase in technical complexity or cost.

According to a first aspect of the invention a process is proposed to this effect for the detection of abnormal situations of a person in a living place, especially for remote surveillance of elderly people, characterised in that it comprises the following steps:

receiving information supplied by a sensor worn by the person and relative to at least one vital variable of the person, receiving information originating from a series of motion sensors provided in different places of the living place, and confronting said information with predetermined rules involving timeouts established as a function of the place and of the time of day, and in response to the preceding step, launching or not abnormal situation signalling.

This results in the discrimination of abnormal situations that can be coded in an extremely fine manner, especially according to the characteristics of the living place, living habits of the person, etc.

According to a second aspect, a process for the detection of abnormal situations of a person in a living place is proposed, especially for remote surveillance of elderly people, characterised in that it comprises the following steps:

receiving information supplied by a sensor worn by the person and relative to at least one vital variable of the person, receiving information originating from a series of motion sensors provided in different places of the living place, and confronting said information with predetermined rules involving different timeouts according to whether an anomaly has been detected at the level of the vital variable, and in response to the preceding step, triggering or not an abnormal situation signalling.

The invention thus allows modification of surveillance modalities as soon as an abnormal event (fall, rise in heart rate, etc.) has been detected.

According to a third aspect, the invention proposes a process for the detection of abnormal situations of a person in a living place, especially for remote surveillance of elderly people, characterised in that it comprises the following steps:

receiving information supplied by a sensor worn by the person and relative to at least one vital variable of the person, receiving information originating from a series of motion sensors provided in different places of the living place, and confronting said information with predetermined rules involving timeouts, according to a common process relaunched at each arrival in a new place where there is no existing abnormal situation, and in response to the preceding step, triggering or not abnormal situation signalling.

A simple process for executing with a common algorithm during different life phases in the living place is realised accordingly.

Some preferred, though non-limiting, aspects of these processes are the following:

in the processes of the second and third aspects, the timeouts can differ according to the time of day, just as the timeouts can have different values according to the place where a presence of the person is detected.

the process is suitable for signalling two levels of abnormal situation.

the two levels of abnormal situation are determined by two situations of absence of movement during two distinct timeouts.

an abnormal situation of the highest level is determined either by the elapsing of two distinct timeouts without movement, or by detection of an anomaly at the level of the vital variable with the elapsing of at least one timeout without movement.

the sensor worn by the person comprises a kinematic sensor.

the sensor worn by the person comprises a cardiac rhythm sensor.

the process is executed in the central unit of a pre-existing alarm system fitted with presence sensors.

The invention finally proposes a system for the detection of abnormal situations of a person in a living place, especially for the remote surveillance of elderly people by execution of a process such as defined in the preceding, characterised in that it comprises in combination:

a central unit, a plurality of motion sensors suitable for providing information on movement to the central unit, a sensor worn by the person and suitable for providing information relative to at least one vital variable of the person to the central unit via a wireless communication channel, a clock connected to the central unit and suitable for providing information on time of day and timeout, a teletransmission device for sending alerts to a remote surveillance station, the central unit comprising means for controlling the teletransmission device as a function of determined combinations of information originating from the motion sensors, from the sensor worn by the person and from the clock.

Some preferred aspects of this system are the following:

the sensor worn by the person comprises a kinematic sensor.

the sensor worn by the person comprises a cardiac rhythm sensor.

the clock is suitable for developing timeouts of different values according to the place and the time of day.

the clock is suitable for developing timeouts of different values according to whether an anomaly has been detected at the level of the vital variable.

the control means are suitable for carrying out a common process relaunched at each arrival in a new place where there is no existing abnormal situation.

Other aspects, aims and advantages of the present invention will emerge from the following detailed description of a preferred embodiment of the latter, given by way of non-limiting example and given in reference to the attached figures, wherein.

The following will describe a remote surveillance system of persons based on:

one or more fall detectors sensitive to the movements of the body of the person;

presence detectors placed in the different rooms of the place where the person is living, typically the domicile, consideration of the time elapsed since the last detection of presence, consideration of the moment of the day in which it occurs.

The idea underlying this combination is essentially that the information supplied by the fall detector does not have the same "importance" according to whether it occurs for example in the bedroom or the bathroom, at night or during daytime, and according to whether it is followed by prolonged inactivity or, on the contrary, normal activity is resumed.

Figure 1:
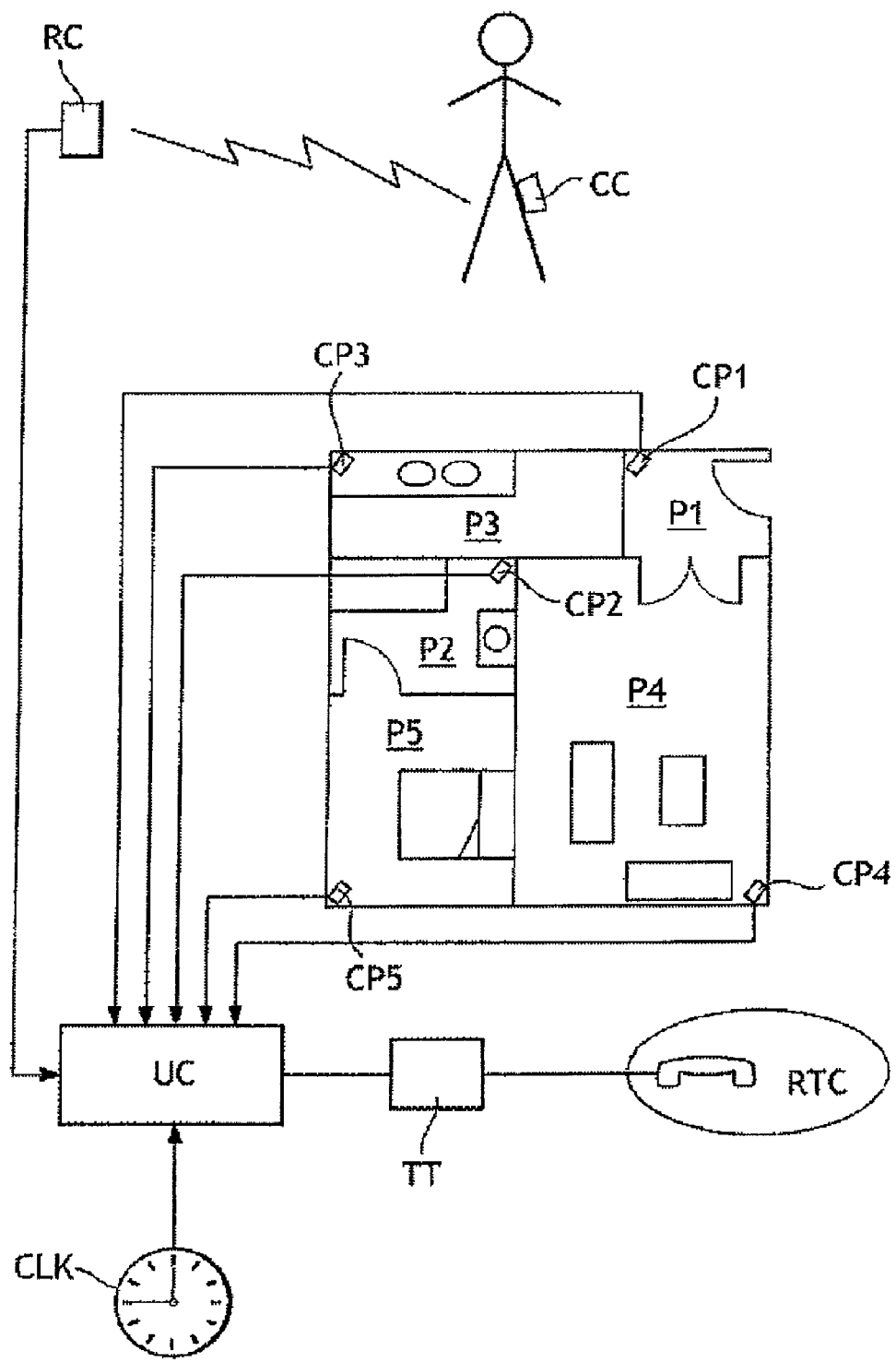
FIG. 1 is a schematic view of a system according to the present invention.

In the living place of the telesurveilled person, and in reference to FIG. 1, the system according to the invention comprises to this effect a central processing unit CPU connected to a receiver RC communicating via a wireless channel with a sensor such as a kinematic fall sensor CC worn by the person (for example fixed on the thigh) and with a plurality of presence detectors, here numbering five, DP1, DP2, ..., DP5, situated in the different rooms P1, P2, ... P5 of the living place, and fitted with a permanent CLK clock time stamp device.

As an alternative to the fall sensor or in complement thereto, any other sensor can be provided, which can be worn by the person and is able to deliver information on a vital variable of the person (for example a cardiac rhythm sensor, arterial pressure sensor, etc. and more generally of any variable sensed on the human body and able to correlate with the state of health).

The system is also fitted with communication means such as a teletransmitter TT for sending messages to a remote surveillance centre, for example via the switched telecommunications network RTC or even via a wireless telephone network such as cellular, preferably by following protocols used by telealarm professionals.

Of course, the system is designed to be sufficiently robust and reliable to guarantee a 24/7 service in all situations (feed cut, problems on the telephone network, etc.).

Accordingly, the system of the invention is preferably based on a telealarm platform rather than on a platform of personal computer type, the reliability of which is substantially inferior.

In a preferred though non-limiting embodiment, the execution of the present invention can be based on a device known by the brand name "QUIATIL+" (registered trademark) and sold by the French company Intervox Systèmes.

This device is capable of relaying alarms originating from several alarm insets worn by persons to a remote surveillance centre by borrowing a line from the switched telecommunications network RTC.

Algorithmic Aspects

The functionalities of the system of the invention in terms of determining anomaly or alarm situations are described here by finished state automatons in which the following stable states can be defined:

Normal (all is well),

Doubt or anomaly (it is suspected that something abnormal is happening),

Alarm (a serious situation has been detected),

Return to normal (an abnormal situation had been detected but doubt was discounted in favour of a return to a normal situation).

Passing from one stable state to another is done via a transition which is triggered when a combination of conditions (here Boolean conditions, 0 or 1 or true/false) is fulfilled (change of room by the person, fall signal, etc.).

According to the invention it is possible to take into account the time elapsed from the clearing of a transition by means of timeout variables. The conditions also take into account different moments of the day by defining Boolean variables originating from cutting up, in a fixed or vague manner, periods of the day (for example night, morning, afternoon, evening).

Finished State Machine

As mentioned earlier, the internal states of the system can be represented in a finished state machine whereof the transitions depend on the last room occupied, on the time of day and on the level of activity of the person, in turn determined by timeouts.

In this respect, an in-depth study of the person's behaviour determined that various situations by a single automaton model, parameters of which depend on the context, could be considered.

Figure 2:
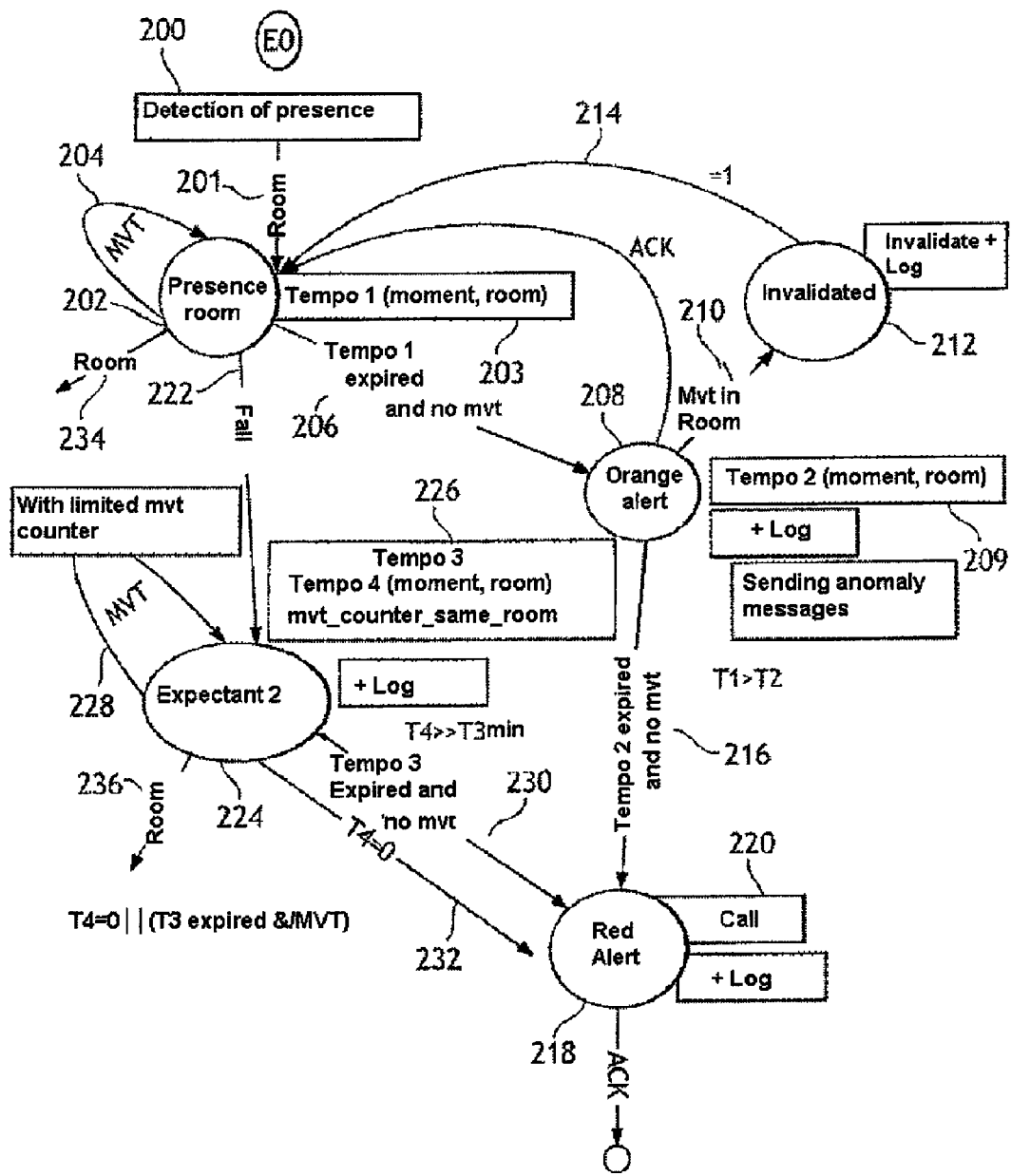
FIG. 2 is a sketch of a generic finished state automaton which can be used in the system of the present invention.

In reference to FIG. 2, there now follows a description of an automaton titled "Room" from which a program capable of being executed by the central processing unit can be written by the person skilled in the art using simple routine operations.

Example

IF "the state present is valid" AND "the conditions of the transition are fulfilled"

THEN

"the preceding state is invalidated" AND "the new state is validated" AND "the actions corresponding to the new state are undertaken".

A program example is provided in attachment to the present description.

Adjustment Process

Adjusting the state machine of FIG. 2 and of the corresponding program supplied in attachment is advantageously done by a particular simulation process, executed this time on an ordinary computer platform of PC type and which will now be described.

General Principle

The aim of the simulator is to evaluate the pertinence of an algorithmic development and have it confront different types of scenarios of various severity levels.

It instantaneously knows the algorithm's "response" confronted to a proposed scenario.

To simplify scenario development, use is made of a semi-natural language, structured by "tags" and following simple syntactic rules.

For example, the following scenario:

```
<scenario>
12:14:02,Bedroom
12:14:03,Fall
12:14:36,Bedroom
12:14:37,Living room
12:14:47,Living room
18:22:50,Living room
</scenario>
``` signifies that a presence has been detected at 12 h 14 min 02 sec in the room "bedroom", that in the following second the fall sensor sent an alarm, followed by a period of inactivity of 33 seconds, until such time as a new sign of activity in the bedroom is noticed, followed by entry to the living room a second later, and more regular activity in this room.

It can be supposed that the subject has fallen in the bedroom, lost consciousness for a few seconds and has painfully moved to the living room where the subject tried to get attention.

An advantage of such a scenario in the context of the present invention is that it can be written without any computer knowledge and transcribed directly by means of simple text-editing software. Preferably, a scenario designer can be supported on a specific user interface using simple actions to create more or less complex scenarios, over more or less long periods, and which further develop a scenario in a controlled manner, either in "real time", or "step-by-step", with a vision of the successive states taken by the state machine.

A scenario file is structured in two parts:

the configuration parameters delimited by configuration tags (<config>, </config>)

the description of the scenario, delimited by scenario tags (<scenario>, </scenario>), with an event tag for each event of the scenario (hh:mm, room, event).

The user interface has three main options:

a) System Configuration—the simulator must be configured according to the characteristics of the living place for which the scenarios will be tested. A configuration user interface is thus provided for defining:

1) the list of rooms in an apartment, 2) the precise moments of the beginning and the ending of periods of the day, 3) the durations of a certain number of timeouts peculiar to each of the rooms and periods, which populates a table of the following type:

| | Tempo1 | | | | Tempo2 | | | | Tempo3 | | | | ... |
|---|---|---|---|---|---|---|---|---|---|---|---|---|---|
| | Morning | Anytime | Evening | Night | Morning | Anytime | Evening | Night | Morning | Anytime | Evening | Night | ... |
| Room1 | | | | | | | | | | | | | |
| Room2 | | | | | | | | | | | | | |
| Room3 | | | | | | | | | | | | | |
| ... | | | | | | | | | | | | | |
| RoomN | | | | | | | | | | | | | |

All of these data are stored in a structured file (tag) whereof attachment B of the present description gives an example, with the initialisation part between the tags (<config>, </config>) and the scenario part between the tags (<scenario>, </scenario>). It is evident here that the different values of timeouts can simply be read in the corresponding locations of the structure, or again calculated (for example it can be provided that a short timeout is a determined fraction of a long timeout itself stored).

b) Scenarios Input

The input user interface of the scenarios preferably comprises buttons, specifically a series of 5 buttons for inputting the lines of the scenario, or: hh:mm, room, event, continuationcontinuation, endend, and a button for displaying the created scenario, preferably using a commercially available text-editing tool (for example Wordpad, registered trademark).

c) Launching of the Simulation

The user interface also launches the simulation by allowing the user to identify the scenario (access path), and to select the mode "real time" or "step-by-step". The simulator then displays the values resulting from execution of the scenario, for example in the form of a table, as follows:

| Clock | Room | Event | State | Message |
|---|---|---|---|---|
| 08:40:02 | kitchen | | presence | |

Implementation

As indicated earlier, possible and currently preferred implementation of the invention is realised by contributing novel functionalities to the remote surveillance platform "QUIATIL+" (registered trademark) sold by the French company Intervox, and more particularly novel functionalities of interpreting information originating from the sensors arranged in the system (fall sensor CC on the person and presence detectors CPn arranged in the different zones), with a view to determining the state of the telesurveilled person among three pre-defined states:

normal state, non-vital alert (e.g.: abnormal nocturnal walking, abnormally prolonged standing, etc.), vital emergency alert (fall, serious illness, etc.).

Main Functionalities

As indicated earlier, the process according to the invention is preferably constructed around a finished state automaton of the type illustrated in FIG. 2 and whereof each change of state is induced by the data of the sensors and the time data in particular comprising the timeouts and the moments of the day.

The implemented functions are the following:

a) function timeout "TempoX": time loop with emission of a signal on expiration of the time limit. The time limit is a parameter of the function, taking its values in an interval for example of 1 minute to 24 hours; the expiration signal is sent asynchronously to the functioning of the program of the central processing unit, either via an interruption, or via an event synchronisation message.

b) "Clock" function: function which returns the information "moment of the day" as a function of the information delivered by the internal clock CLK to the platform; the output variable "moment of the day" belongs to a list of 4 elements (whole value or enumerated type={morning, afternoon, evening, night}).

c) "MVT" movement function: Boolean function with threshold that takes the value 1 when there is movement or 0 for no movement. There is "movement" if an event detected by a presence sensor CPn occurred since less than x seconds for the same location; on the contrary there is absence of movement if the time limit since the last event sensed is greater than or equal to x seconds; this function can be built on a model of guard dog type which is composed of a timeout of fixed duration and a zero-reset device which must be activated before lapse of the timeout; the parameter, optionally adjustable during configuration of the system, is placed in a stored memory zone (Flash), with also the possibility of remote modification via the telephone network.

d) "Room" function: function which signals that a zone change has just occurred and updates the current occupied zone; the event signal is positioned (that is, set to 1) during an event originating from a presence sensor if this sensor is different to the current sensor (specifically the sensor having sent the preceding presence event), signalling a change in location. Its value is reset to zero by the automaton function to be described hereinbelow; the value of the occupied zone belongs to a list of N elements (whole or enumerated variable).

e) "Fall" function: function which signals that the fall sensor CC has detected a fall;

f) "Automaton" function: function which calculates the new state of the automaton according to the current state and to the event which has just occurred. This function is responsible for making the decisions and taking the actions of each entry, in a new state.

Beyond these functions, the system includes communications functions ("Call" function) to a remote control centre (server of the telealarm control station), and mainly transmission of alert messages (anomaly or alarm) to the remote surveillance centre, with expectation of confirmation (by the remote materiel or, better, by the staff of the remote surveillance centre). It also includes a logging function "Log" consisting of registering the different events and actions in a database stored in the central unit CPU.

Communications Between the Pre-existing Alarm System and the System of the Invention The program which animates the system of the present invention, executed in the central unit CPU, makes calls to the pre-existing program of the alarm system, also executed in the central unit, to:

obtain the values of the timeouts, given here that if there are N zones to monitor and if a day is cut up into P periods, there are N×P values (the unit being the minute in the present example, with a value between 1 and 1440 minutes to cover a time window of 24 hours;

obtain the value of the "movements" timeout, preferably coded in seconds with a value between 1 and 65535 (coding on 16 bits);

be informed on external events which occur on the different channels corresponding to the presence detectors and the fall sensor;

supply messages intended to be placed in the events log, with the appropriate coding;

finally, supply the alarm messages which must be sent by the TT teletransmitter to the remote surveillance centre.

On the practical implementation level, the person skilled in the art will be able to design such a user interface as a function of the specifications of the processing system housing the intelligence of the system of the present invention. In the present example, the person-monitoring program communicates with the program of the commercial system QUIATIL+ by way of a revolving data buffer (file) in which the events have just been written, is as much as they happen, in the form:

[Time/Event/Number]

where

Time is a word of 32 bits expressing elapsed time, in seconds, from an arbitrarily fixed initial date.

Event is a coding octet of the event type, and, for example, of events 'e'=external channel, 't'=tempo, 'a'=remote confirmation.

Number is a word of 16 bits which indicates the number of the event or of the timeout, for example according to the following allocation:

| | |
|---|---|
| E 0 | Fall sensor |
| E 1 | IR entry |
| E 2 | IR bedroom |
| E 3 | IR lounge |
| E 4 | IR kitchen |
| E 5 | IR WC |
| E 6 | IR bathroom |
| T 0 | Tempo MVT due |
| T 1 | Tempo 1 due |
| T 2 | Tempo 2 due |

-continued

| T 3 | Tempo 3 due |
| T 4 | Tempo 4 due |
| A 0 | Distant confirmation |

Again in reference to FIG. 2 an example of execution of the invention will now be described and, more precisely, which events result in which changes of state and how the alerts of first level (anomaly) and of second level (alarm) are generated.

Detection of presence by a presence sensor CPn in the room Pn (reference 200) leads, via the function Room 201, to the "presence room" state 202. The timeout Tempo1 is launched in 203. Movements within this room without the timeout Tempo1 expiring signify normal activity of the person monitored, and the "presence room" state continues via the function MVT 204.

When the timeout Tempo1 expires during which no new movement in the room has been detected by the sensor CPn, the corresponding function 206 leads to the "Orange Alert" state 208.

If a new movement is detected prior to expiration of a timeout Tempo2 launched in 209 on arrival in the "Orange Alert" state 208, then the function MVT/Room 210 leads to the "Invalid" state 212 followed by a return to the "Presence Room" state 202 via a transition 214.

If in the "Orange Alert" state 208, on expiry of the timeout Tempo2, no movement is detected, then the corresponding function 216 leads to the "Red Alert" state 218 where a "Call" function 220 signalling to the remote surveillance centre is triggered.

If the fall sensor CC now gives a fall signal in the state 202, then the "Fall" function 222 leads to a so-called "Expectant" state 224 where two timeouts Tempo3 and Tempo4 are launched in 226.

Movements detected in this state prior to expiration of the timeout Tempo3 leave the state machine in the same state (transition 228). However, absence of movement during this period leads, via the corresponding function 230, to the "Red Alert" state 218 described earlier.

Similarly, the Timeout Tempo4, of longer duration than Tempo3, leads via the transition 232 to the above state 218 even if movements have been detected in this room. This effectively detects prolonged presence in the same room following an anomalous situation (first level). This can correspond for example to the case of a person in difficulty, but still slightly mobile, who is trying to draw attention for help, for example by waving the arms.

It is also evident from FIG. 2 that from the "Presence Room", "Orange Alert" and "Expectant" states, a "Room" type function (234 or 236 in particular) can lead the state machine to the "Presence Room" state 202, but corresponding to another room of the living place, fitted in particular with its own timeouts Tempo1 to Tempo4, where these, as already mentioned, are able to have different values according to the moments of the day and able to be specific to the room in question. It is noted here that different machines states can also be provided according to the rooms of the living place, according to the expected behaviour of the person in each type of room ("normal" behaviour in a living room is different to "normal" behaviour in a kitchen, a bathroom, a bedroom, etc.), in the case where the choice of different timeout values according to the rooms does not treat all scenarios.

Advantageously, a change of room also causes a zero-reset of the "Fall" information. It can nevertheless be provided that fall information produced in a certain room and logged, combined with an absence of movement in the next room, can cause an "Orange Alert".

It is also noted that the "Log" function is executed especially in "Orange Alert", "Expectant", "Red Alert" and "Invalid" states so as to register all the events which have occurred, as mentioned hereinabove.

It is noted also that a "Yellow Alert", of a level of severity less than that of an "Orange Alert" could be triggered if high frequencies of occurrence of the "fall" signal followed by a so-called "Expectant" state are noted in the log which are followed neither by an "Orange Alert" state, nor by a "Red Alert" state, and this during a predetermined period, for example several times per period of 24 hours.

Finally, it is noted that an ACK confirmation is necessary after a call resulting from the "Red Alert" state and the return to the "Presence Room" state following the "Orange Alert" state.

Numerous modifications can of course be made to the performance of the state machine and to the corresponding program.

Similarly, numerous modifications can be made as to the types of signals detected, which can go beyond fall detection and detection of presence room by room.

Attachment A: Example of Program in Algorithmic Language

```
//configurations
clock=00:00
Tempo1=0
Tempo2=0
Tempo3=0
Tempo4=0
Counter_movement=0
Counter_movement_max=4
Movement=1
room=new-room=bedroom
shifting=O
Event=0
//Update of entries
Open file (scenario)
Read file (scenario)
Read the list of tempos
Read the list of rooms
Read the scenario
Read the clock of the scenario
Read the clock_following of the scenario
Moment=Determining the moment (Night, Morning,
Afternoon, Evening) room=scenario (room)
Tempo1=Tempo1 (room, moment)
event=scenario (event)
state=presence
As long as there is an event to be processed
{
According to (state)
{
   case presence:
   if (Tempo1 ==0 ) then if ( MVT==0) then
   state=alert_orange
       Tempo2=Tempo2 (room,moment)
       Log(state, room, clock, tempo1)
               Envoi_message("...")
   or else
   Tempo1=tempo1 (room, moment)
   Log (state, room, clock, tempo1)
     Endif
   Or else
    Tempo1-1
   Endif
```

-continued

```
Project GATEM Final Report
    if (event=Fall) then state=state_expectant
        Tempo4=Tempo4(room, moment)
        Tempo3=Tempo3(room, moment)
log (state, room, clock, tempo1)
endif
    case alert_orange:
if (MVT==1 || shifts=1) then
    Log ("Invalid State", room, clock)
    state=presence
    Tempo1=Tempo1 (room, moment)
    BREAK;
if (Tempo2 ==0 ) then state=alert-red
    Log (state, room, clock)
    Send_message (" " )
or else
Tempo2 −1
Endif
    case expectant:
if (Tempo4==0) then state=alert-red
        log (state, room, clock)
        break;
or else
Tempo4−1
endif
If (Tempo3 ==0) then if (MVT ==0) then
    state=alert-red
        log (state, room, clock)
    or else        // Cpt_tempo3 − 1
        Tempo3=Tempo3 (room, moment)
Endif
Or else
tempo3 − 1
        endif if
if (shifting=1) then state=State_presence
tempo1=tempo1 (room, moment)
endif
break
    case alert_red:
if (ACK==1) then fall=0
state=presence
Tempo1=Tempo1 (room)
    default:
log ("Internal error")
    break;
} end according to (state)
clock+1;
Moment= Determine the moment (Night, Morning, Any Time, Evening)
if (clock=clock_following) then
    Counter_movement=Counter_movement_max
    Movement=1
    If (event != "Ack" and event !="Fall") then
    Room_before=Room
    Room=event
    If (room_before==room_following) then
        Room=room_following
        Shift=1
    Or else
    Shifts=0
    Endif
or else
    Counter_movement= −1
    if Counter_movement==0 then movement=0 endif
endif
} end WHILE (1)
```

Attachment B: Example of Scenario

```
<--fall morning, appart. 6 rooms-->
<config>
<list_rooms>
bedroom, kitchen, living room, toilets, bathroom, entry
<moment night, morning, any time, evening>
22-8, 8-12, 12-18, 18-22
<tempo_1>
5 45 120 120
5 45 360 360
5 45 45 45
5 45 60 60
480 45 120 30
5 15 15 15
<tempo_2>
10 10 10 10
10 10 10 10
10 10 10 10
10 10 10 10
10 10 10 10
10 10 10 10
<tempo_3>
10 10 10 10
10 10 10 10
10 10 10 10
10 10 10 10
10 10 10 10
10 10 10 10
<tempo_4>
360 360 360 360
360 360 360 360
360 360 360 360
360 360 360 360
360 360 360 360
360 360 360 360
</config>
<scenario>
07:50, bedroom
07:51, bedroom
07:52, kitchen
08:06, bathroom
08:10, fall
08:30, ack
</scenario>
```

The invention claimed is:

1. A process for the detection of abnormal situations of a person in a living place, especially for remote surveillance of elderly people, characterised in that it comprises the following steps:
receiving information supplied by a sensor worn by the person and relative to at least one vital variable of the person,
receiving information originating from a series of motion sensors provided in different places of the living place,
confronting said information with predetermined rules involving timeouts, wherein said predetermined rules are selected from a group of rules consisting of rules involving timeouts established according to place and time of day, rules involving different timeouts according to whether an anomaly has been detected at the level of the vital variable and rules involving timeouts according to a common process relaunched at each arrival in a new place where there is no existing abnormal situation, and
in response to the preceding step, triggering or not an abnormal situation signalling,
wherein said process is suitable for signalling two levels of abnormal situation and wherein an abnormal situation of the highest level is determined either by the elapsing of two distinct timeouts without movement, or by detection of an anomaly at the level of the vital variable with the elapsing of at least one timeout without movement.

2. The process as claimed in claim 1, wherein said predetermined rules involve timeouts established according to place and time of day.

3. The process as claimed in claim 1, wherein said predetermined rules involve different timeouts according to whether an anomaly has been detected at the level of the vital variable.

4. The process as claimed in claim 1, wherein said predetermined rules involve timeouts according to a common process relaunched at each arrival in a new place where there is no existing abnormal situation.

5. The process as claimed in claim 1, characterised in that the timeouts differ according to the time of day.

6. The process as claimed in claim 1, characterised in that the timeouts have different values according to the place where a presence of the person is detected.

7. The process as claimed in claim 1, characterised in that the timeouts have different values according to predefined behaviour of the person in said place.

8. The process as claimed in claim 1, characterised in that the two levels of abnormal situation are determined by two situations of absence of movement during two distinct timeouts.

9. The process as claimed in claim 1, characterised in that the sensor worn by the person comprises a kinematic sensor.

10. The process as claimed in claim 1, characterised in that the sensor worn by the person comprises a cardiac rhythm sensor.

11. The process as claimed in claim 1, characterised in that it is carried out in the central unit of a pre-existing alarm system fitted with presence sensors.

12. The process as claimed in claim 1, characterised in that it comprises an initial configuration step including carrying out a behaviour simulation process.

13. A system for detection of abnormal situations of a person in a living place, especially for remote surveillance of elderly people by the execution of the process as claimed in any one of the preceding claims, characterised in that it comprises in combination:
a central unit,
a plurality of motion sensors suitable for providing motion information to the central unit,
a sensor worn by the person and suitable for providing information relative to at least one vital variable of the person to the central unit via a wired communications channel,
a clock connected to the central unit and suitable for providing information on time of day and timeout, and
a teletransmission device for sending alerts to a remote surveillance station, the central unit comprising means for controlling the teletransmission device as a function of combinations of determined information originating from motion sensors, from the sensor worn by the person and from the clock,
characterised in that the device further comprises confrontation means of said information with predetermined rules using timeouts established as a function of at least one of the following parameters:
place and time of day,
the fact that an anomaly has been detected at the level of the vital variable, and
arrival of the person in a new place where no abnormal situation exists,
wherein said system is suitable for signalling two levels of abnormal situation and wherein an abnormal situation of the highest level is determined either by the elapsing of two distinct timeouts without movement, or by detection of an anomaly at the level of the vital variable with the elapsing of at least one timeout without movement.

14. The system as claimed in claim 13, characterised in that the sensor worn by the person comprises a kinematic sensor.

15. The system as claimed in claim 13, characterised in that the sensor worn by the person comprises a cardiac rhythm sensor.

16. The system as claimed in claim 13, characterised in that the clock is suitable for developing timeouts of different values according to the place and time of day.

17. The system as claimed in claim 13, characterised in that the clock is suitable for developing timeouts of different values according to whether an anomaly has been detected at the level of the vital variable.

18. The system as claimed in claim 13, characterised in that the control means are suitable for carrying out a common process relaunched at each arrival in a new place where there is no existing abnormal situation.

19. The system as claimed in claim 13, characterised in that it further comprises configuration means by means of a behaviour simulation process.

* * * * *